United States Patent [19]

Tarvin

[11] Patent Number: 4,641,524
[45] Date of Patent: Feb. 10, 1987

[54] OPTICAL HUMIDITY SENSOR

[75] Inventor: Jeffrey A. Tarvin, Ann Arbor, Mich.

[73] Assignee: KMS Fusion, Inc., Ann Arbor, Mich.

[21] Appl. No.: 765,727

[22] Filed: Aug. 15, 1985

[51] Int. Cl.$^4$ .............................................. G01W 1/00
[52] U.S. Cl. ...................................... 73/335; 73/336.5
[58] Field of Search ...................... 73/335, 336, 336.5; 356/369; 250/231 R

[56] References Cited

U.S. PATENT DOCUMENTS

| | | | |
|---|---|---|---|
| 3,192,426 | 6/1965 | Feuer | 73/336.5 |
| 3,528,278 | 9/1970 | Sterling | 73/336.5 |
| 3,926,052 | 12/1975 | Bechtel | 73/336.5 |
| 3,972,619 | 8/1976 | Stevens | 356/369 |
| 4,083,249 | 4/1978 | Gerber | 73/336.5 |
| 4,539,521 | 9/1985 | Matsumoto | 250/231 R |

FOREIGN PATENT DOCUMENTS

| | | | |
|---|---|---|---|
| 2938434 | 11/1980 | Fed. Rep. of Germany | 73/335 |
| 1547507 | 11/1968 | France | 73/336.5 |
| 112636 | 9/1981 | Japan | 73/336 |
| 397830 | 11/1974 | U.S.S.R. | 73/336.5 |
| 855589 | 8/1981 | U.S.S.R. | 73/335 |
| 881588 | 11/1981 | U.S.S.R. | 73/335 |
| 928214 | 5/1982 | U.S.S.R. | 73/335 |
| 945837 | 7/1982 | U.S.S.R. | 73/335 |

*Primary Examiner*—Stewart J. Levy
*Assistant Examiner*—Hezron E. Williams
*Attorney, Agent, or Firm*—Barnes, Kisselle, Raisch, Choate, Whittemore & Hulbert

[57] ABSTRACT

An optical dielectric humidity sensor which includes a dielectric mirror having multiple alternating layers of two porous water-adsorbent dielectric materials with differing indices of refraction carried by a translucent substrate. A narrow-band polarized light source is positioned to direct light energy onto the mirror, and detectors are positioned to receive light energy transmitted through and reflected by the mirror. A ratiometer indicates humidity in the atmosphere which surrounds the dielectric mirror as a function of a ratio of light energies incident on the detectors.

17 Claims, 2 Drawing Figures

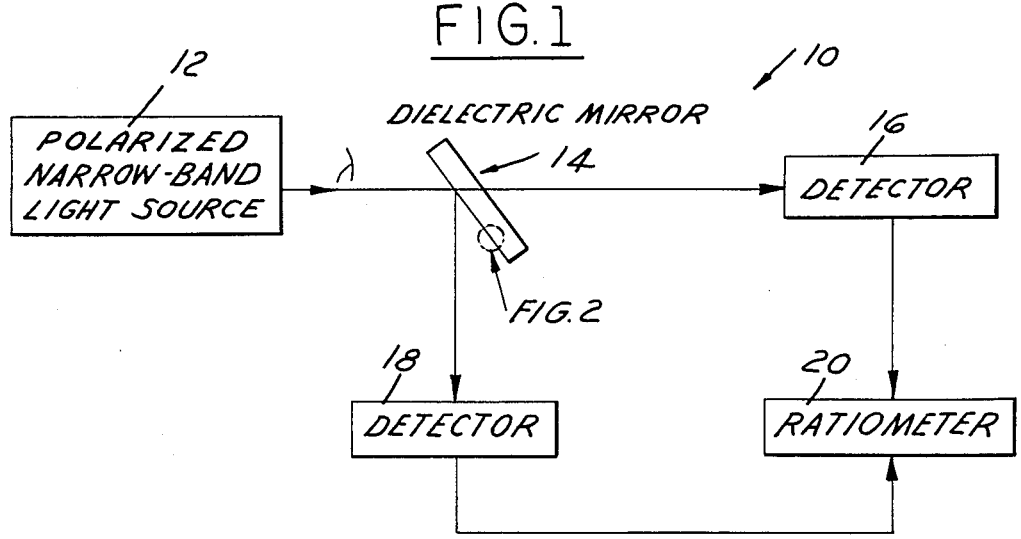
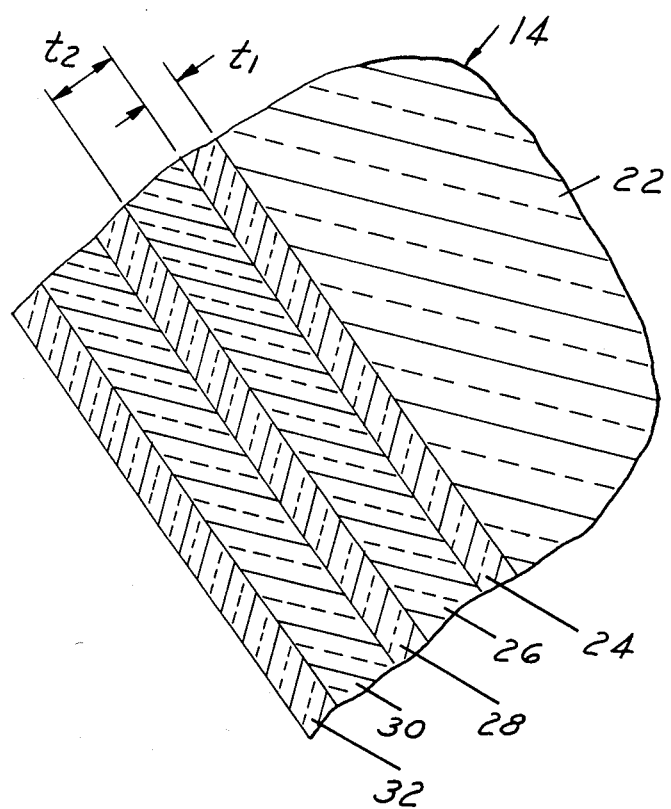

OPTICAL HUMIDITY SENSOR

The Government has rights to this invention pursuant to Contract No. DE-AC02-84ER80144 awarded by the U.S. Department of Energy.

The present invention is directed to an optical sensor for indicating humidity in a surrounding atmosphere.

A general object of the present invention is to provide a sensor for indicating humidity in a surrounding atmosphere which is inexpensive to manufacture and install, which is accurate over an extended operating lifetime, which may be readily calibrated by unskilled or semi-skilled personnel, and which is particularly well adapted for measuring humidity in a hazardous environment.

The invention, together with additional objects, features and advantages thereof, will be best understood from the following description, the appended claims and the accompanying drawings in which:

FIG. 1 is a schematic drawing of an optical humidity sensor in accordance with a presently preferred embodiment of the invention; and FIG. 2 is a fragmentary sectional view on an enlarged scale of a portion of the dielectric mirror in FIG. 1.

FIG. 1 illustrates a presently preferred embodiment 10 of an optical humidity sensor in accordance with the invention as comprising a narrow-band light source 12, such as a laser or LED, which transmits light energy at a nominal wavelength $\lambda$ along a preselected light path. A dielectric mirror 14 is positioned to intercept light from source 12, and to transmit a first portion thereof onto a first optical detector 16 while reflecting a second portion thereof onto a second optical detector 18. Detectors 16,18 may include suitable lenses, fiber optics, collecting reflectors or the like for focusing light energy onto a photocell so as to provide a detector output signal which varies as a function of intensity of light incident on the detector. The outputs of detectors 16,18 are fed to a ratiometer 20 for indicating humidity in the atmosphere which surrounds dielectric mirror 14 as a function of a ratio of the detector output signals. The ratiometer may include suitable electronic components for producing an output signal which is linearly related to humidity. It is preferable that light source 12 be polarized since reflectivity of mirror 14 depends upon polarization of light incident thereon.

Referring to FIG. 2, dielectric mirror 14 preferably comprises a flat translucent substrate 22 of silicate or other glass composition having multiple layers 24–32 of dielectric material deposited or otherwise coated thereon. Layers 24–32 preferably comprise alternating layers of two dielectric materials having differing indices of refraction, layers 24,28 and 32 being of a first dielectric material and of substantially identical thickness, and intermediate layers 26,30 being of a second material and substantially identical thickness. Material layers 24,28,32 have a relatively high index of refraction, while layers 26,30 have a lower index of refraction. It is desirable to maximize the index of refraction difference between the differing layers, all other factors being equal, in order to accommodate a greater range or spread of wavelengths from light source 12. It is presently envisioned that the index of refraction of layers 24,28,32 should be greater than 1.95, while the index of refraction of layers 26,30 should be less than 1.5. (The index of refraction of silicate glass substrate 22 is about 1.45.) Each layer should be on the order of $\frac{1}{4}$-wavelength thick. That is, the thickness t1 of layers 24,28,32 should be substantially equal to the nominal wavelength $\lambda$ of light source 12 divided by four times the corresponding index of refraction. In the same manner, the thickness t2 of layers 26,30 should be substantially equal to the wavelength $\lambda$ divided by four times the corresponding index of refraction. Since the index of refraction of layers 26,30 is less than that for layers 24,28,32, the thickness t2 is correspondingly greater than the thickness t1.

Material layers 24–32 may be deposited or coated on substrate 22 using any suitable process, such as vapor deposition, rf sputtering or electron-beam deposition processes. Thicknesses of the material layers previously set forth are nominal design thicknesses, with tolerances varying according to manufacturing processes employed. Typical high-index materials for layers 24,28,32 include $TiO_2$, $ZrO_2$ and $ZnS$. Typical low-index materials for layers 26,30 include $SiO_2$, $MgF_2$ and $Na_3AlF_6$. All of these materials are sufficiently porous for use in the optical dielectric humidity sensor of the invention.

In general, operation of the invention is based upon the principle that reflectivity/transmissivity of dielectric mirror 14 varies with the amount of water vapor adsorbed by dielectric layers 24–32. Porous dielectric materials, of the type noted by way of example above, readily adsorb vapor from the environment surrounding the mirror, so that the ratio of light reflected by and transmitted through mirror 14 accurately reflects humidity in such surrounding environment. A particular advantage of employing ratiometer in accordance with the preferred embodiment of the invention is that, while the absolute change in reflectivity or transmissivity may be small for a small change in humidity, the ratio change will be large. That is, since the reflectivity may be on the order of ninety-nine percent, a small fractional change in reflectivity will result in a large fractional change in transmissivity, and thus a large fractional ratio change.

It will be appreciated that the five dielectric layers shown in FIG. 2 are for illustrative purposes only. Additional alternating layers may be required in actual practice of the invention. It is also envisioned that the principles of the invention may be embodied in a window having a dielectric anti-reflection coating. In this embodiment, the transmissivity would be large and the reflectivity would undergo a large fractional change in response to a small change in relative humidity. In either case, the sensitivity and dynamic response of the sensor can be changed by altering porosity of the dielectric films.

The invention claimed is:

1. A humidity sensor comprising porous dielectric means for adsorbing moisture from a surrounding atmosphere, a narrow-band light source for directing light energy onto said dielectric means at preselected nominal wavelength, said porous dielectric means comprising at least one layer of porous dielectric construction having quarter-wave thickness as a function of said preselected nominal wavelength and index of refraction of said porous dielectric construction, and means positioned to intercept light energy incident on said dielectric means from said source for indicating humidity in the atmosphere surrounding said dielectric means as a function of variations in light transmission/reflection characteristics of said dielectric means.

2. The humidity sensor set forth in claim 1 wherein said dielectric means comprises a translucent substrate having said at least one layer of dielectric material positioned to intercept light energy from said source.

3. The humidity sensor set forth in claim 2 wherein said dielectric means comprises a translucent substrate having multiple layers of dielectric material carried thereon, successive ones of said layers having differing indices of refraction.

4. The humidity sensor set forth in claim 3 wherein said multiple layers comprise alternate layers of two dielectric materials having differing indices of refraction.

5. The humidity sensor set forth in claim 4 wherein said two dielectric materials comprise a first material having an index of refraction greater than 1.95 and a second material having an index of refraction less than 1.5.

6. The humidity sensor set forth in claim 5 wherein said first material is selected from the group consisting of $TiO_2$, $ZrO_2$ and $ZnS$, and wherein said second material is selected from the group consisting of $SiO_2$, $MgF_2$ and $Na_3AlF_6$.

7. The humidity sensor set forth in claim 6 wherein said substrate is of silicate glass composition.

8. The humidity sensor set forth in claim 4 wherein each said layer has a thickness of substantially $\lambda/4n$, wherein $\lambda$ is said nominal wavelength and $n$ is index of refraction of said layer.

9. The humidity sensor set forth in claim 3 wherein said means positioned to intercept light energy comprises means positioned to receive light energy transmitted through said dielectric means.

10. The humidity sensor set forth in claim 3 wherein said means positioned to receive light energy comprises means positioned to receive light energy reflected by said dielectric means.

11. The humidity sensor set forth in claim 3 wherein said means positioned to receive light energy comprises first means positioned to receive light energy transmitted through said dielectric means, second means positioned to receive light energy reflected by said dielectric means, and third means coupled to said first and second means for indicating humidity as a combined function of light energy transmitted and reflected by said dielectric means.

12. The humidity sensor set forth in claim 11 wherein said third means comprises means for indicating humidity as a function of a ratio of said transmitted and reflected light energies.

13. A humidity sensor comprising dielectric means having at least one layer of dielectric material for adsorbing moisture from a surrounding atmosphere, a light source positioned to direct light energy onto said dielectric means at preselected nominal wavelength such that a portion of said light energy is reflected by said dielectric means and another portion of said light energy is transmitted through said dielectric means, said dielectric means comprising at least one layer of porous dielectric construction having quarter-wave thickness as a function of said nominal wavelength and index of refraction of said porous dielectric construction, first light detection means positioned to receive light energy transmitted through said dielectric means, second light detection means positioned to receive said light energy reflected by said dielectric means, and means for indicating humidity of the atmosphere surrounding said dielectric means as a function of light energy detected at said first and second detection means.

14. The humidity sensor set forth in claim 13 wherein said humidity indicating means comprises means responsive to a ratio of light energies received at said first and second detection means.

15. The humidity sensor set forth in claim 14 wherein said dielectric means comprises a dielectric mirror.

16. The humidity sensor set forth in claim 15 wherein said dielectric mirror comprises a translucent substrate having multiple layers of dielectric material carried thereon, successive ones of said layers having differing indices of refraction.

17. The humidity sensor set forth in claim 16 wherein said multiple layers comprise alternate layers of two dielectric materials having differing indices of refraction.

* * * * *